(12) United States Patent
Plasterer et al.

(10) Patent No.: US 10,473,689 B2
(45) Date of Patent: Nov. 12, 2019

(54) PEDOMETER IN A LOW-POWER DEVICE

(71) Applicant: Google LLC, Mountain View, CA (US)

(72) Inventors: Michael R. Plasterer, Los Altos, CA (US); Samuel P. Kho, Mountain View, CA (US)

(73) Assignee: Google LLC, Mountain View, CA (US)

(*) Notice: Subject to any disclaimer, the term of this patent is extended or adjusted under 35 U.S.C. 154(b) by 725 days.

(21) Appl. No.: 14/399,770

(22) PCT Filed: May 7, 2013

(86) PCT No.: PCT/US2013/039923
§ 371 (c)(1),
(2) Date: Nov. 7, 2014

(87) PCT Pub. No.: WO2013/169755
PCT Pub. Date: Nov. 14, 2013

(65) Prior Publication Data
US 2015/0127290 A1  May 7, 2015

Related U.S. Application Data

(60) Provisional application No. 61/643,396, filed on May 7, 2012.

(51) Int. Cl.
| | |
|---|---|
| *G01P 21/00* | (2006.01) |
| *A61B 5/11* | (2006.01) |
| *G01C 22/00* | (2006.01) |
| *G01D 5/12* | (2006.01) |
| *G01P 15/02* | (2013.01) |

(52) U.S. Cl.
CPC ............. *G01P 21/00* (2013.01); *A61B 5/112* (2013.01); *A61B 5/1118* (2013.01);
(Continued)

(58) Field of Classification Search
CPC ........ G01C 21/16; G01C 22/006; G01D 5/12; G01P 15/02; G01P 21/00; A61B 5/1118; A61B 5/112; A61B 5/1123
(Continued)

(56) References Cited

U.S. PATENT DOCUMENTS

| | | | |
|---|---|---|---|
| 8,460,001 B1 * | 6/2013 | Chuang .............. | G09B 19/0038 434/247 |
| 2001/0022828 A1 | 9/2001 | Pyles | |

(Continued)

OTHER PUBLICATIONS

International Search Report issued in corresponding International Application No. PCT/US2013/039923 dated Nov. 25, 2013.
(Continued)

*Primary Examiner* — John E Breene
*Assistant Examiner* — Eyob Hagos
(74) *Attorney, Agent, or Firm* — Lerner, David, Littenberg, Krumholz & Mentlik, LLP

(57) ABSTRACT

Methods and systems for determining a user's steps in portable device include deriving amplitudes from raw sensor data; comparing the amplitudes to an amplitude threshold, and counting a step when one of the amplitudes exceeds the amplitude threshold to obtain a step count; determining a current gait type based on the step count; dynamically adjusting the amplitude threshold in order to reduce effects of swinging movements and false steps; and applying a post filter to the step count based on time between steps and a minimum number of prior consecutive steps to derive a filtered step count that reduces false readings due to short bursts of rapid movement by the user.

29 Claims, 7 Drawing Sheets

(52) U.S. Cl.
CPC .............. *G01C 22/006* (2013.01); *G01D 5/12* (2013.01); *G01P 15/02* (2013.01); *A61B 5/1123* (2013.01)

(58) Field of Classification Search
USPC ....... 702/104, 141, 145, 147, 151, 158, 160; 434/247; 701/472
See application file for complete search history.

(56) References Cited

U.S. PATENT DOCUMENTS

| | | |
|---|---|---|
| 2001/0022858 A1 | 9/2001 | Komiya et al. |
| 2003/0018430 A1* | 1/2003 | Ladetto .................. G01C 21/16 701/472 |
| 2005/0219120 A1 | 10/2005 | Chang |
| 2007/0143068 A1* | 6/2007 | Pasolini ............... G01C 22/006 702/160 |
| 2007/0143069 A1 | 6/2007 | Pasolini et al. |
| 2011/0022352 A1* | 1/2011 | Fujita .................. A61B 5/1036 702/160 |

OTHER PUBLICATIONS

Hache, "Development of a Wearable Mobility Monitoring System"; Thesis—Ottawa—Carleton Institute for Biomedical Engineering; University of Ottawa; 2010; http://www.irrd.ca/cag/smartphone/Hache-Thesis-2010.pdf.

* cited by examiner

PEDOMETER IN A LOW-POWER DEVICE

CROSS-REFERENCE TO RELATED APPLICATIONS

This application claims the benefit of provisional Patent Application Ser. No. 61/643,396, filed May 7, 2012, incorporated herein by reference.

BACKGROUND OF THE INVENTION

A step counter or pedometer is a portable carried by a user that provides an estimate of distanced travelled by foot of a user. Pedometers, which are typically electronic or electro-mechanical device, originally were intended to be worn on a belt are now incorporated into many different types of fitness devices that are worn or carried by users, such as smart phones, watches and bracelets. Conventional pedometers use accelerometers to sense body motion, and based on the body motion count the user's steps. This step count may then be converted into distance using stride length.

One approach for implementing a pedometer may include plotting accelerometer data versus time, and then count a step whenever the accelerometer data exceeds a reference threshold having a predetermined value. While the plot of accelerometer data may have a profile that is similar for each step and may work for certain cases, the approach may result in an inaccurate step count. This is because the accelerometer data pattern varies widely due to a number of factors such as peculiarities in the user's gait, whether the user in a vehicle, and the location of the pedometer relative to the user which may cause erroneous swinging motions, e.g., when worn on a wrist or carried on a backpack.

Today's pedometers may utilize MEMS inertial sensors and sophisticated software to detect steps. These MEMS inertial sensors may have either 1-, 2- or 3-axis detection of acceleration, which permit more accurate detection of steps with fewer false positives. Although there are many software approaches used to analyze the output of the inertial sensor and estimate the step count, typically increased step count accuracy requires increased mathematical calculations. The problem is that these calculations are computationally expensive in terms of both time and processor power and may have an impact on battery life of the device, particularly if the device includes a touchscreen.

Accordingly, what is needed is an improved pedometer function that is capable of filtering out swinging movements and false steps but in a low-power device.

BRIEF SUMMARY OF THE INVENTION

Exemplary embodiments related to methods and systems for determining a user's steps in portable device. Aspects of the exemplary embodiments include: deriving amplitudes from raw sensor data; comparing the amplitudes to an amplitude threshold, and counting a step when one of the amplitudes exceeds the amplitude threshold to obtain a step count; determining a current gait type based on the step count; dynamically adjusting the amplitude threshold in order to reduce effects of swinging movements and false steps; and applying a post filter to the step count based on time between steps and a minimum number of prior consecutive steps to derive a filtered step count that reduces false readings due to short bursts of rapid movement by the user.

BRIEF DESCRIPTION OF SEVERAL VIEWS OF THE DRAWINGS

The drawings illustrate the design and utility of embodiments of the invention, in which similar elements are referred to by common reference numerals. In order to better appreciate the embodiments, reference should be made to the accompanying drawings that illustrate these embodiments. However, the drawings depict only some embodiments of the invention, and should not be taken as limiting its scope. With this caveat, embodiments of the invention will be described and explained with additional specificity and detail through the use of the accompanying drawings in which.

DETAILED DESCRIPTION OF THE INVENTION

The present invention relates to improved methods and systems determining a user's steps. The following description is presented to enable one of ordinary skill in the art to make and use the invention and is provided in the context of a patent application and its requirements. Various modifications to the embodiments and the generic principles and features described herein can be made. Thus, the present invention is not intended to be limited to the embodiments shown, but is to be accorded the widest scope consistent with the principles and features described herein.

In the following description, for purposes of explanation, numerous details are set forth in order to provide a thorough understanding of various embodiments. It is important to note that the invention can be practiced without all of these details. Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The exemplary embodiments relate to methods and systems for implementing a pedometer function in a low-power device in a manner that simplifies necessary calculations while filtering out swinging movements and false steps.

Figure 1:
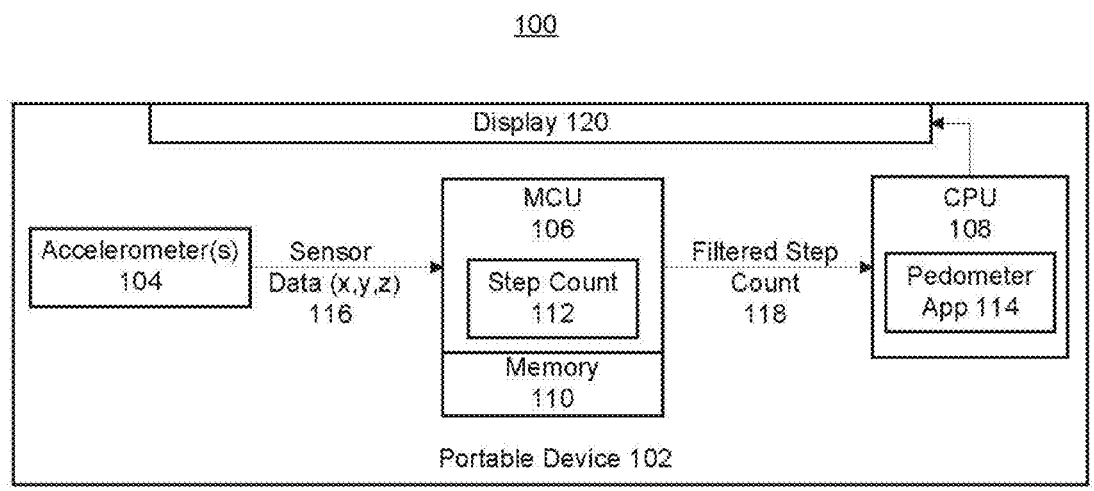
FIG. 1 illustrates a system for implementing a pedometer in a low-power device.

FIG. 1 illustrates a system for implementing a pedometer in a low-power device. The system 100 may include a portable device 102 that includes one or more of the accelerometers 104, a low-computation processor, such as a Micro-Controller Unit (MCU) 106, coupled to the accelerometer 104, a central processing unit (CPU) 108 coupled to the MCU 106, and a display 120 that is coupled to the CPU 108.

The CPU 108 performs high-level functions for the portable device 102 and drives the display 120. In one embodiment, the CPU 108 may comprise an Advanced RISC Machine (ARM) processor or the like. To save power, CPU 108 has wake and sleep modes. The CPU 108 enters sleep mode during periods of inactivity and transitions to wake mode periodically, or in response to user input, and refreshes the display 120. In one embodiment, the MCU 106 is used to perform low-level functions for the portable device 102 so the CPU 108 can remain in sleep mode. As such, the MCU 106 is incapable of performing high-level functions, such as executing Java or driving the display 120. The MCU 106 may also include a memory 110, which may comprise both a flash ROM and RAM, for storing code and threshold values. In one embodiment, the term MCU 106 may be implemented as a DSP or ASIC. As used herein, the term MCU is intended to include such low computation devices.

The accelerometer 104 may comprise a MEMS accelerometer (e.g., a 3-axis accelerometer from ST Microelectronics) that may be used to measure information such as position, motion, tilt, shock, and vibration for use by the MCU 106. Any other type of inertial sensor may also be used. A MEMS inertial sensor may be advantageous because it may be fabricated in a very small size (e.g., 5×5×1 millimeters), consume very little power, and still be sensitive to gestures.

According to one aspect of the exemplary embodiment, calculation of step counts is performed within the MCU 106 rather than the CPU 108 to save power. During operation of the portable device 102, the MCU receives raw sensor data 116 in the form of X, Y, Z values corresponding to each dimension. The MCU executes a step count component 112 that calculates filtered step counts 118 a manner that simplifies calculations while effectively filtering false steps and swinging movements.

As the CPU 108 transitions from sleep mode to wake mode, the CPU 108 receives the filtered step counts 118 and executes a pedometer application 114 that uses the filtered step counts 118 to calculate step rate and step length. From these values, the pedometer application 114 further calculates any combination of distance traveled, speed, calories and pace for output to the display 120. In one embodiment, the pedometer application 114 may be implemented using Java™ or other programming language.

In one embodiment, the portable device 102 may represent any type of electronic device capable of incorporating a pedometer function, including a cell phone, a portable game device, a media player, a digital camera, a tablet, and the like. In an exemplary embodiment, the portable device 102 may comprise a wearable portable device, such as the one described with respect to FIGS. 5A and 5B.

Figure 2:
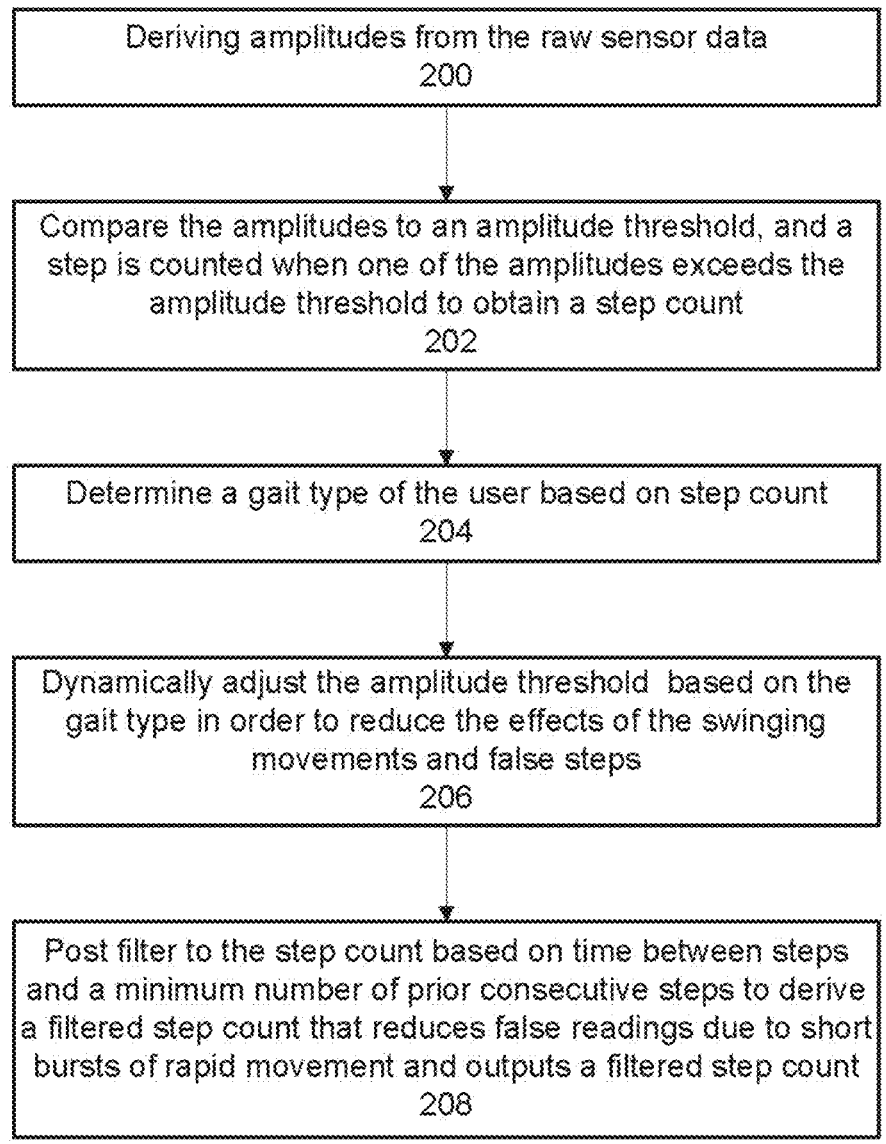
FIG. 2 is a block diagram illustrating a process for counting a user's steps performed by the step count component in the MCU.

FIG. 2 is a block diagram illustrating a process for counting a user's steps performed by the step count component 112 in the MCU 106. In one embodiment, the process may begin by deriving amplitudes from the raw sensor data (block 200). A series of amplitudes over time include values that may vary widely. According to one aspect of the exemplary embodiment, in order to reduce extraneous amplitudes, the step count component 112 may further normalize or smooth the amplitudes using a current amplitude and at least one previous amplitude to generate smoothed amplitudes. The step count component 112 may then detect peaks and troughs from the smoothed amplitudes, as described further below.

The amplitudes are compared to an amplitude threshold, and a step is counted when one of the amplitudes exceeds the amplitude threshold to obtain a step count (block 202).

The step count component 112 also attempts to reduce false peaks in the amplitudes by using the step count to determine a gait type of the user (block 204). The gait type is then used to dynamically adjust the amplitude threshold in order to reduce effects of swinging movements and false steps (block 206).

The step count component 112 may further apply a post filter to the step count based on time between steps and a minimum number of prior consecutive steps to derive a filtered step count 118 that reduces false readings due to short bursts of rapid movement by the user and outputs a filtered step count 118 (block 208).

Figure 3:
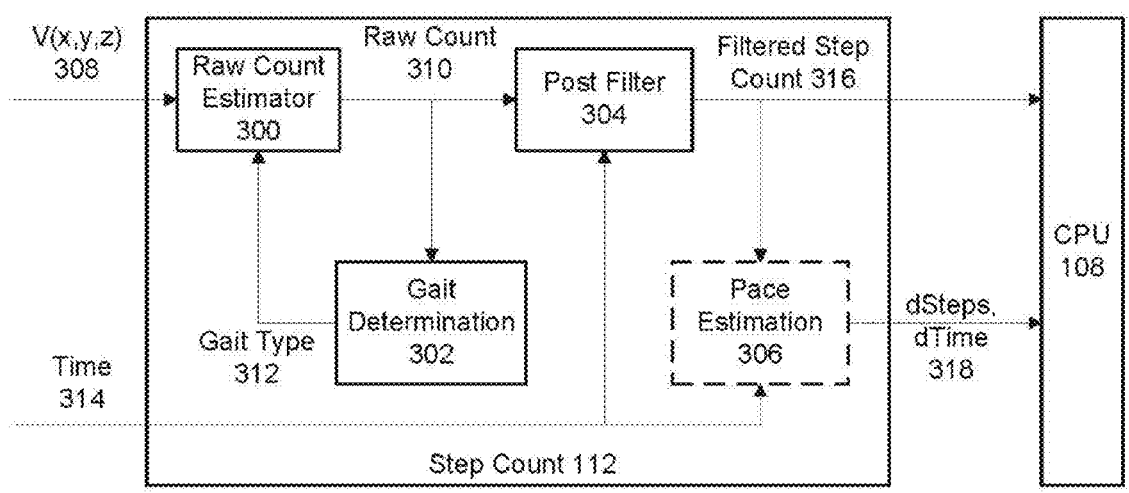
FIG. 3 is a block diagram illustrating additional details of the step count component.

FIG. 3 is a block diagram illustrating additional details of the step count component 112. In one embodiment, the step count component 112 may include raw count estimator 300, a gait determination component 302, a post filter component 304 and an optional pace estimation component 306.

According to one aspect of the exemplary embodiment, all calculations performed by the step count component 112 use fixed-point arithmetic rather than floating point arithmetic, which the MCU 106 may be incapable of due to low processing power.

The raw count estimator 300 receives a stream of raw sensor data as acceleration X,Y,Z values 308. In one embodiment, the acceleration X,Y,Z values 308 may be 12-bit numbers, representing −2G . . . +2G, and may be sampled periodically, e.g., approximately every 40 ms (25 Hz), or every 20-60 ms.

The acceleration X,Y,Z values 308 may be composited into a single magnitude value:

$$M^2 = X^2 + Y^2 + Z^2$$

The raw count estimator 300 derives a magnitude vector $V=M^2$, which according to one aspect of the exemplary embodiment, is represented as a squared value, rather than a square root to minimize necessary computations. This is the same as treating [X,Y,Z] as a vector and deriving magnitude. Because square root is an expensive operation, the raw count estimator 300 performs calculations using the squared magnitude.

As the magnitude vectors V are derived, the raw count estimator 300 normalizes or smooths the vectors to reduce ups and downs in the curve. That is done by maintaining a queue of previous magnitude vectors and combining them with a current magnitude vector. In this embodiment, weights are assigned to the current magnitude vector and one or more previous magnitude vectors. In one embodiment, where two previous magnitude vectors (prev and prevprev) are used, a smoothed magnitude vector may be obtained by:

$$\text{Smoothed } V = (5*\text{current} + 2*\text{prev} + 1*\text{prevprev})/8$$

In this embodiment, the smoothed magnitude vectors are generated using a weighting of 5:2:1, e.g., the current vector is assigned 50%, the previous vector is assigned 20%, and 1% is assigned to the vector before that. The result of adding the weighted vectors is divided by 8. The assigned weightings and the denominator of 8 are chosen to allow cheap computation. For example a divide by eight may be implemented in the MCU 106 using a simple shift-right by three decimal points so that very little processing power is required. Of course, other values besides eight could be used in this operation. Below, the term V is intended to refer to the smoothed value.

Next, the raw count estimator 300 detects peaks and troughs from the smoothed magnitude vectors to determine whether the smoothed magnitude vectors are trending up or down. Trends in the smoothed magnitude vectors moving up or down may be used to indicate footsteps. For example, if the portable device 102 is worn on a user's wrist, and the user moves the arm in a figure eight pattern, then the M value could be 0.8-1.0, for example and close to linear because the values go up and then go down and when taken in aggregate, may flatten out. But if the user is walking, then somewhere in the plot, the data will trend up because of the footstep jars the arm. These values are arrhythmic. Peak and trough detection is therefore necessary to determine if the smoothed magnitude vectors are trending upward or trending downward.

Plotting the smoothed magnitude vectors versus time, a trough is a local minimum, and a crest a local maximum. To find local minimum or maximum, calculus could be used to take a derivative and set it to zero. However, such an operation would be computationally expensive. Therefore, the peak and trough detection is simplified by the raw count estimator 300 as follows:

1) Keep track of previous V.
2) If current V is greater than previous V, then set ascending mode. If current V is less than previous V, then set descending mode. If current V is the same as previous V, ignore current V and do not change mode.
3) If in descending mode and switched to ascending mode, then determine a trough has been found. If in ascending mode and switched to descending mode, then determine a peak has been found, where the actual trough or crest is the previous V.

After peak detection, the raw count estimator 300 performs amplitude detection to analyze the amplitudes of the ups and downs in the data. Amplitude is calculated based on the difference between a peak and its preceding trough. The raw count estimator 300 compares the amplitude of the peaks and troughs to an amplitude threshold, rather than a value to a value threshold. Each time an amplitude exceeds the amplitude threshold, the raw count estimator 300 counts a step and outputs a raw count 310 to the gait determination component 302 and the post filter component 304.

The gait determination component 302 is used to create a feedback loop with the raw count estimator 300 to dynamically adjust the amplitude threshold based on a gait type 312 detected from the raw count 310. The gait determination component 302 is used to factor in the user's gait into the raw count 310 determination because if the user is walking too slowly, the amplitudes will be arrhythmic and will not meet predetermined amplitude thresholds, which the step will not be counted. Thus, the gait determination component 302 determines whether the user is going slow or fast, assigns a gait type, and feeds the gait type back to the raw count estimator 300 to help improve the accuracy of the peak and trough determination of future raw counts.

The exemplary embodiment creates multiple amplitude thresholds for different gait types to produce accurate step counts. For example, one amplitude threshold assigned to a gait type for walking (GAIT_WALK), another amplitude threshold is assigned to a gait type for fast walking (GAIT_FASTWALK), another amplitude threshold is assigned to a gait type for running (GAIT_RUN), and another amplitude threshold may be assigned to unknown gait types (GAIT_UNKNOWN), as shown in Table 1.

TABLE 1

| Gait Type | Gait Amplitude Thresholds |
|---|---|
| GAIT_UNKNOWN | 20000 |
| GAIT_WALK | 26000 |
| GAIT_FAST_WALK | 30000 |
| GAIT_RUN | 145000 |

In one embodiment, the gait types and corresponding amplitude threshold are stored in memory 110 of the MCU 106 in a table. The raw count estimator 300 may then use a gait type 312 assigned by the gait determination 302 to perform a table look up to obtain the corresponding amplitude threshold. Note that In one embodiment, the thresholds may be 16.16 fixed-point numbers.

In one embodiment gait determination component 302 may determines the gait type 312 using the following heuristic.

1) Keep track of the past amplitudes (e.g., 10-20) using a FIFO queue, where the oldest one is dropped as a new one is added.
2) Of these past amplitudes, count the number of small amplitudes (nSmalls) and the number of big amplitudes (nBigs).
3) If nBigs>2*nSmalls, then set the gait type to GAIT_RUN.
4) If nSmalls>2*nBigs, then set the gait type to GAIT_WALK.
5) Otherwise, if there's a mixture, and nBigs>3 and nSmalls>3, then set the gait type to GAIT_FAST_WALK (if nBigs<4 or nSmalls<4, then it is considered not enough data to set the gait type to fast walk).
6) Otherwise, set the gait type to GAIT_UNKNOWN.

The post filter component 304 attempt to eliminate false steps (super extraneous data) by determining whether motions are too fast or too slow based on the raw count 310. The post filter component 304 may be based on the following assumptions.

The first assumption is that false steps are likely to be far apart. When the user moves there arm while sitting down and that movement happens to look like a step, it will be a while until the next time the arm is moved again that also gets miscounted. At least, it will be a while longer until the next time, compared to the shorter time between steps when the user is truly walking.

Therefore, according to one embodiment, the post filter component 304 receives time 314 as input and uses the time 314 to examine elapsed time between each of the potential steps in the raw count 310. This elapsed time may be referred to as DELTA_T, and is compared to a time threshold referred that may be referred to as MAX_DELTA_T. If an elapsed time between a step in the previous step is less than MAX_DELTA_T, and the current step is determined to be a candidate step. If an elapsed time between a current step and the previous step is greater than MAX_DELTA_T, then the current step is determined to be a false step. In one embodiment, the post filter component 304 may also compare elapsed time between the current step and the previous step to a minimum time threshold which may be referred to as MIN_DELTA_T, but MAX_DELTA_T is considered more crucial.

The second assumption made by the post filter component 304 is that true steps are likely to be continuous. In addition, not only are true steps close together in time, they also tend to arrive in a stream. When the use walks, the user typically walks many steps continuously so the steps come consecutively. The use in unlikely to walk 3 steps, pause for 30 seconds, then walk 2 steps. And were the user to do so, there is little ability to filter out such steps.

Therefore, according to one embodiment the post filter component 304 requires a minimum number of consecutive candidate steps (steps that pass the less than MAX_DELTA_T test) before the candidate steps are counted as true steps. This may be accomplished by determining whether a number of consecutive candidate steps is greater than a consecutive steps threshold, which may be referred to as MIN_CONSECUTIVE. If so, the candidate steps are counted as true steps.

For example, if MIN_CONSECUTIVE is 8, then steps 1, 2, 3, . . . 7 are considered candidate steps, and the output of the post filter component 304 is zero at this stage. When the 8th consecutive candidate step is counted, then these candidate steps are counted as true steps and output as the filtered step count 316. So the filtered step count 316 jumps from zero to 8, then increases to 9, 10, 11, etc. If there is a pause in the candidate steps (i.e., the MAX_DELTA_T test failed), then the next step is considered the 1st step of 7 candidate steps again.

In one embodiment, the thresholds of the post filter component 304 may be configured as shown in Table 2,

TABLE 2

| MIN_DELTA_T | 7, Step Rate of 3.6 Hz (~9.7 m/s, or 22 MPH) |
|---|---|
| MAX_DELTA_T | 40, Step Rate of 0.625 Hz (~0.4 m/s, or 0.9 MPH) |
| MIN_CONSECUTIVE | 8 |

The pace estimation component 306 may be optionally performed while the CPU 108 is in sleep mode. In another embodiment, the pace estimation component 306 is inactive, and when the CPU 108 transitions to wake mode, the CPU 10 receive the filtered step count 316 and performs the pace estimation.

In operation, the pace estimation component 306 receives the filtered step count 316 and time 314 as inputs in order to calculate pace. There are at least two forms of pace one can be measured, overall pace, and instantaneous pace. In one embodiment, the pace estimation component 306 is configured to estimate instantaneous pace, or more accurately, the pace of the very recent past, while overall pace is computed by the pedometer app 114 on the CPU 108 without MCU 106 support.

In one embodiment, whenever the post filter component 304 produces a new filtered step count 316, the filtered step count 316 may be paired with a timestamp:

<FilteredStepCount,TimeStamp> and the pair is fed to a FIFO queue.

In one embodiment, this is accomplished by the paste estimation component 306 determining whether a time between filtered step count 316 outputs is greater than a time threshold (e.g., HOLDING_TIME). If so, the most recent filtered step count 316 is paired with a new timestamp and fed to the FIFO. By only feeding a new pair when there is a new filtered step count 316, the FIFO does not need to be large to obtain good results. By also feeding a pair when there is no new count but some HOLDING_TIME has elapsed, a decay-to-zero effect is obtained if the user stops walking/running.

Whenever a <FilteredStepCount, TimeStamp> pair is fed to the FIFO, and the FIFO is full, the oldest pair in the FIFO is removed. At this point, the FIFO will have:

<countNewest, timeNewest> // just fed to FIFO
<countOldest, timeOldest> // just removed from FIFO The pace estimation component 306 may then compute pace, in steps/time, as:

(countNewest−countOldest)/(timeNewest−timeOldest)

The difference in the filtered step counts (countNewest−countOldest) may be referred to as Delta steps (dSteps) and the difference in the timestamps (timeNewest−timeOldest) may be referred to as Delta time (dTime) (e.g., in the last N seconds, the step count was X).

Division is an expensive operation for the MCU 106. Therefore, in one embodiment, the pace estimation component 306 outputs dSteps and dTime 318 to the pedometer app 114 on the CPU 108 so the pedometer app 114 can perform the division operation. In an alternative embodiment, no time stamp is necessary if the filtered step count 316 is output periodically to the CPU 108. Therefore, the timestamp may be implemented as an actual time stamp or an implied timestamp. The pedometer app 114 can also factor in a steps/mile, possibly adjusted to each user, to turn the filtered step count into an MPH figure.

In one embodiment, Delta time can be zero, meaning there is not enough information yet to calculate a Pace. The pedometer app 114 may check for this and avoid the division if so. On the display 120, the pace could be displayed as "--" in this case.

Example settings for the pace estimation threshold in one embodiment may be:

| FIFO_SIZE | 8 |
|---|---|
| HOLDING_TIME | 5000 |

Pedometer App 114

From the filtered step count 316, the pedometer app 114 may calculate step rate and length, distance, speed, calories, and pace, and makes this data available to a user through a GUI on the display 120 and/or audibly. More specifically, the CPU determines a user's speed by measuring a step rate from steps counted over time; and calculates the speed as a log of the step rate.

Step length and distance traveled may be calculated based on the height of the user. For example, Step length may be calculated as a delta from a base value determined from a height of the user, and distance traveled may be calculated using the user's height and step rate to estimate a change in stride length as the speed changes.

Literature on human biomechanics and user studies show a reasonably high correlation between an individual's height and their normal stride length. Further, as speed increases, there is a corresponding increase in both stride length and stride rate in a fairly predictable pattern—linear over walking speeds of 1.0 to 2.0 m/s, and somewhat more complex over a broader range of speeds. The terms Stride length and Step length can be confusing as Stride length is formally the distance between two successive footfalls of the same foot (e.g., Right foot to Right foot) or twice the Step Length distance. For the purposes of this disclosure, the terms Step Length and Step Rate will be used.

Speed is very simply determined using the formula: Speed=Step Rate×Step Length. However, with only one variable measurable by the MCU 106—steps counted over time—the pedometer app 114 must rely on additional variables, assumptions, and formulas.

Figure 4A:
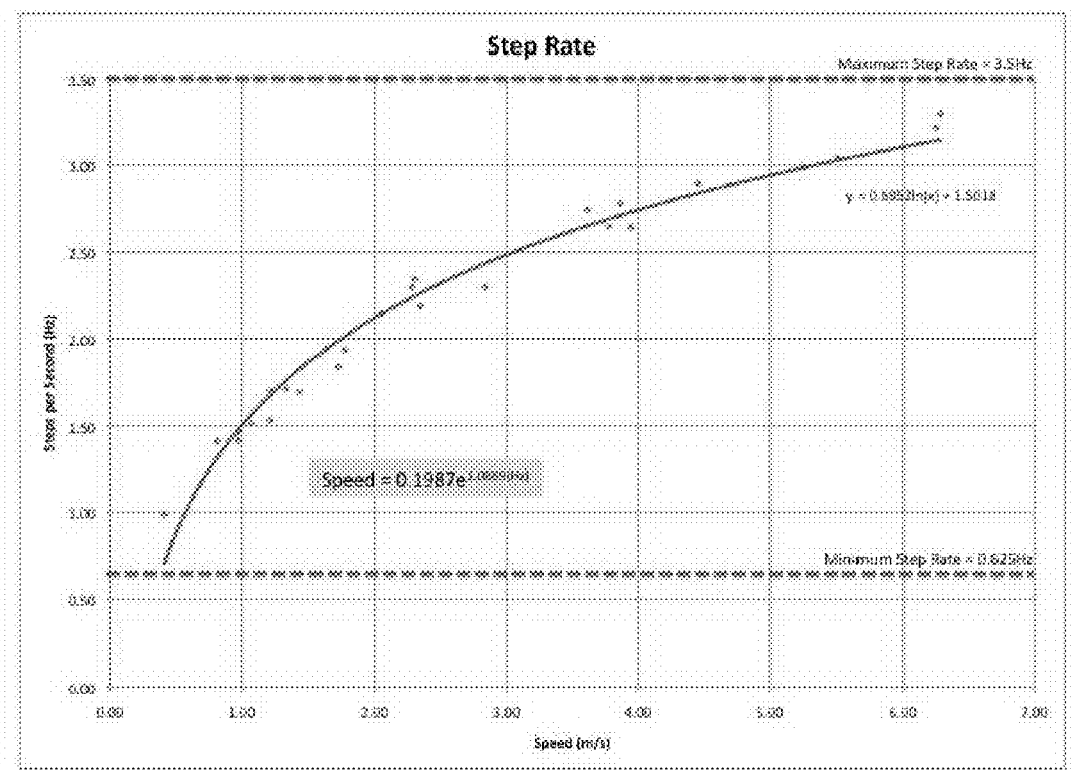
FIG. 4A is a diagram illustrating a Step Rate plot showing testing summary results over a wide range of human speeds ranging from slow walking to fast running or sprinting.

In general, the pedometer app 114 calculates the following based on Step Rate and user settings:
1) Measure Step Rate derived from the filtered step count 118 (i.e., steps counted over time);
2) Calculate Speed using a Step Rate formula;
3) Calculate Step Length—a delta from a base value determined from user height;
4) Calculate Calorie expenditure; and
5) Display Steps, % Goal, Distance, Calories, Session Time, Average Speed and Pace Step Rate FIG. 4A is a diagram illustrating a Step Rate plot showing testing summary results over a wide range of human speeds from slow walking to fast running. Data for the plot in excess of 2 m/s was measured empirically with multiple repetitions for four individuals ranging in height from 160-185 cm, 5'3" to 6'1". The x-axis represents speed (m/s), while the y-axis represents steps per second (Hz).

Numerous best fit algorithms were used to derive the simplest formula relating Step Rate (Hz) over a large range of human speeds, with the results shown in the graph. A Speed formula was determined from a separate plot with the axis values reversed. In one embodiment, with some variability due to differences in subject height, a reasonably accurate speed can be determined for all users based on a log of the step rates as shown.

$$Speed = 0.199 e^{1.089 \, (Hz)}$$

Reasonable upper and lower limits may be set to eliminate seemingly erratic results for the user. For example, in one embodiment, maximum and minimum step rate limits may be set to:

Maximum StepRate=3.5 Hz, approximately 9.7 m/s (22 MPH)

Minimum StepRate=0.625 Hz, approximately 0.4 m/s(0.9 MPH)

Step Length

Unlike Step Rate, Step Length is significantly influenced by the height of an individual, especially at normal walking speeds of 1-2 m/s. And though the best way to determine average Step length (SL) for an individual is to count the number of steps over a set distance, one exemplary embodiment calculates a reasonably close approximation for a person walking at slow speed using the formulas:

$SL\_base = Height \times 0.415$, male $SL\_base = Height \times 0.413$, female where the base "slow walking speed" is set to approximately 1 m/s (~2.2 MPH).

To simplify Step Length calculations, a single linear regression could be applied over all speeds, but could result in either underestimating distances at normal walking speeds or significantly over estimating at fast speeds.

Figure 4B:
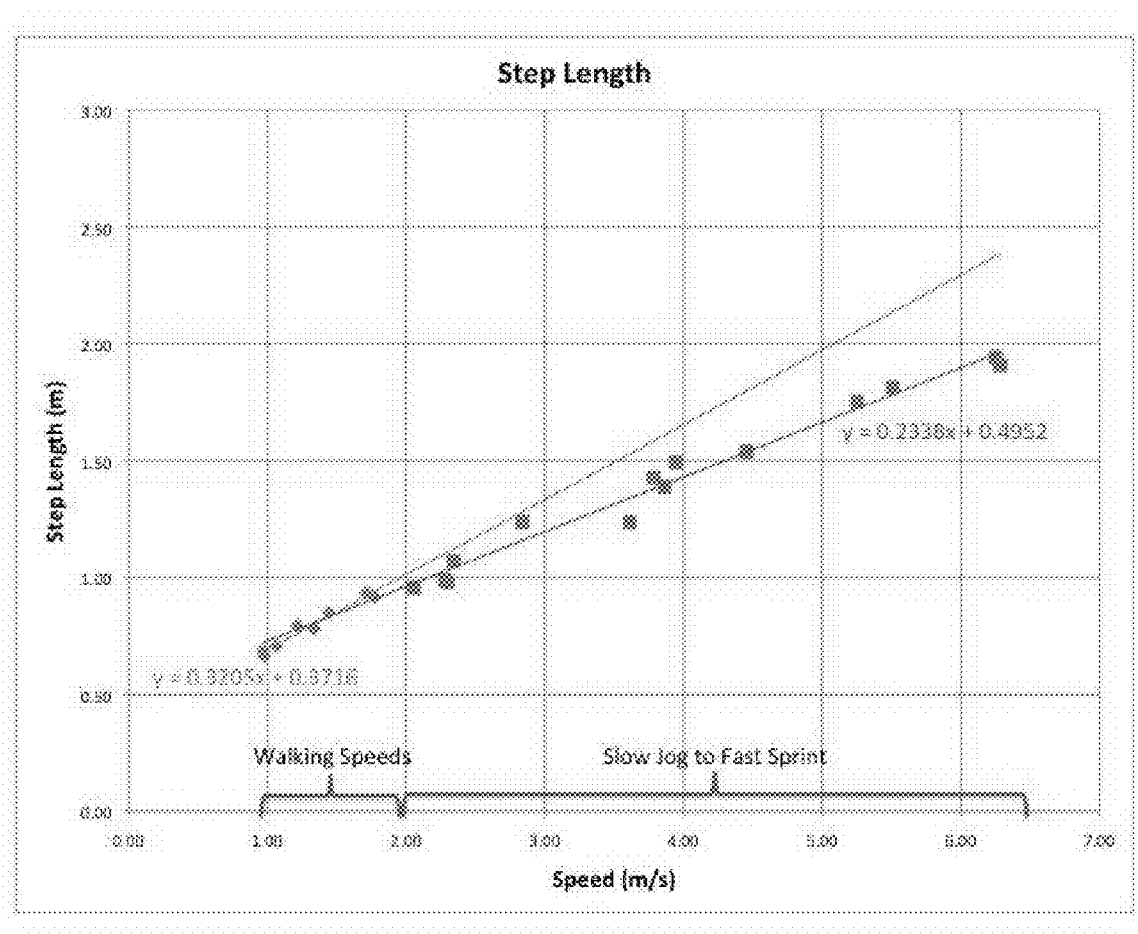
FIG. 4B is a diagram illustrating a plot of regressions for two arbitrary sets of data broken into Walking Speeds and Running Speeds.

FIG. 4B is a diagram illustrating a plot of regressions for two arbitrary sets of data broken into Walking Speeds and Running Speeds. The x-axis is speed (m/s) and the y-axis is step length (meters). Splitting the data into Walking Speeds from 1 m/s to 2 m/s and Running Speeds from 2 m/s to 6.5 m/s allows for application of a simple slope adjustment to determine the relative Step Length (SL) at various speeds fairly accurately. Setting break points at 1 m/s and 2 m/s as shown simplifies the math even further.

The following calculations assume speeds in meters/sec (m/s) and lengths in meters (m):

Walking Speed≤1 m/s //assuming Speed and SL go to zero

Steph Length(SL)=Speed×SL_base

Walking Speed>1 m/s, ≤2 m/s

SL=SL_base+[0.32×(Speed−1 m/s)]

Running Speed>2 m/s

SL=SL_base+0.32+[0.23×(Speed−2 m/s)]

Calorie Calculations

Calorie consumption is complex series of interactions, but can be simplified for the purposes of pedometer app 114 reporting. In one embodiment, the pedometer app 114 may report the calorie burn in excess of a user's resting metabolic rate of approximately 1 kcal/kg/hour while sitting quietly. This is referred to as one (1) MET or Metabolic Equivalent of Task.

Examples of MET values for various types of activities include:

| Physical Activity | MET |
| --- | --- |
| Sleeping | 0.9 |
| Watching television | 1.0 |
| Writing, desk work, typing | 1.8 |
| Walking, 2.5 mph (4 km/h) | 2.9 |
| Cycling, <10 mph (16 km/h) | 4.0 |
| Jogging, general | 7.0 |
| Jumping rope | 10.0 |

Using published values from research on MET measures, two linear regression formulas may be used to derive the MET based on speed.

Figure 4C:
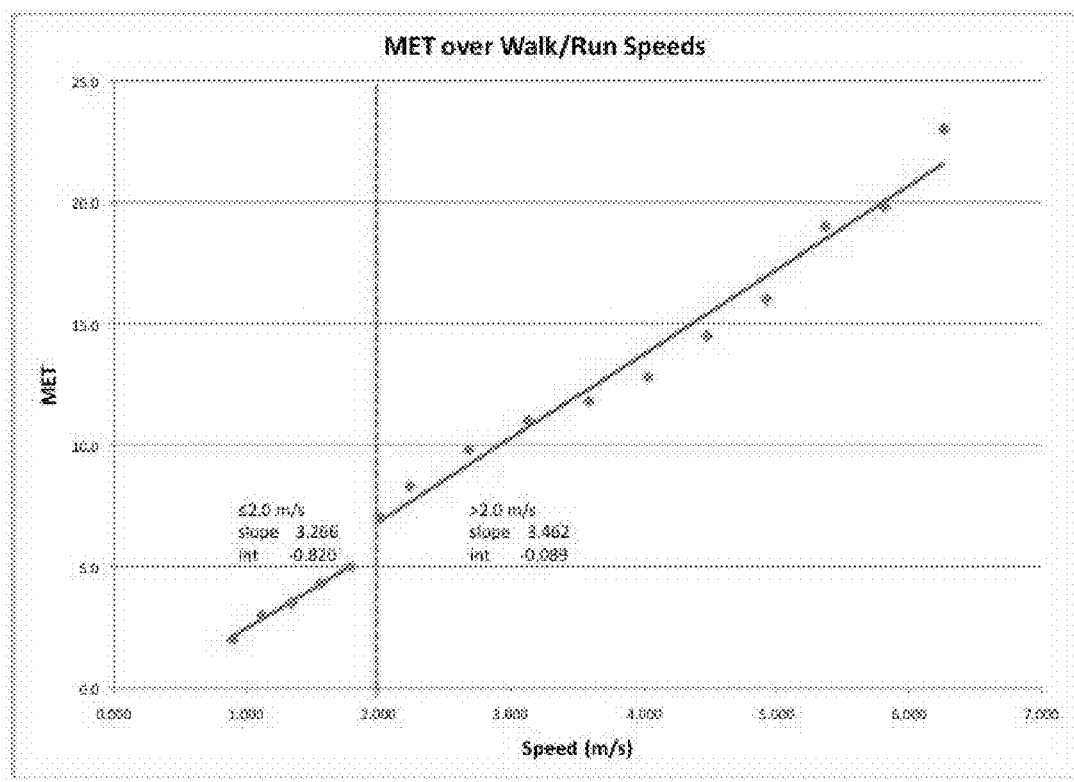
FIG. 4C is a diagram of a plot showing MET (Metabolic Equivalent of Task) as a function of walk/run speeds.

FIG. 4C is a diagram of a plot showing MET as a function of walk/run speeds. One slope on the left-hand side of the dotted vertical line is for Walking Speeds, and the slope on the right-hand side of the dotted vertical line is for Running Speeds.

MET is then calculated for Walking Speeds≤2 m/s as:

MET=3.3×Speed+(−0.82)

MET is then calculated for Running speeds>2 m/s as:

MET=3.5×Speed+(−0.89)

From the MET value, calorie burn may be determined using the formula:

Calories Burned=Duration (min)×[(MET×3.5×weight (kg))/200]

Given the approximate nature of the regression analyses, a reasonable minimum needs to be set to eliminate potential negative Calorie readings.

Minimum activity level=1.0 MET

Finally, zero (0) steps recorded=0 calories burned, e.g., when the pedometer app 114 is left running while the portable device charging overnight.

The portable device 510 can be wearable, for example, on a user's wrist, upper arm, and/or leg, or may be attached to the user's clothing, and may have the functions of a wristwatch, a wearable display, a portable media player, and/or a mobile telephone in various embodiments.

Figure 5A:
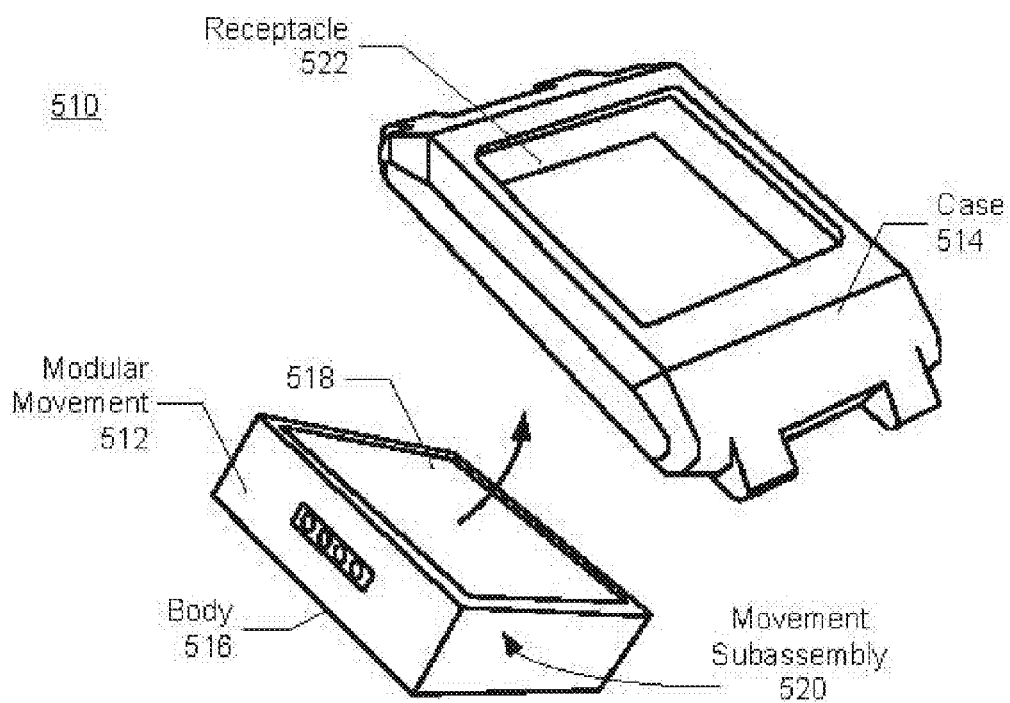
FIGS. 5A and 5B are diagrams illustrating an embodiment of the portable device.
Figure 5B:
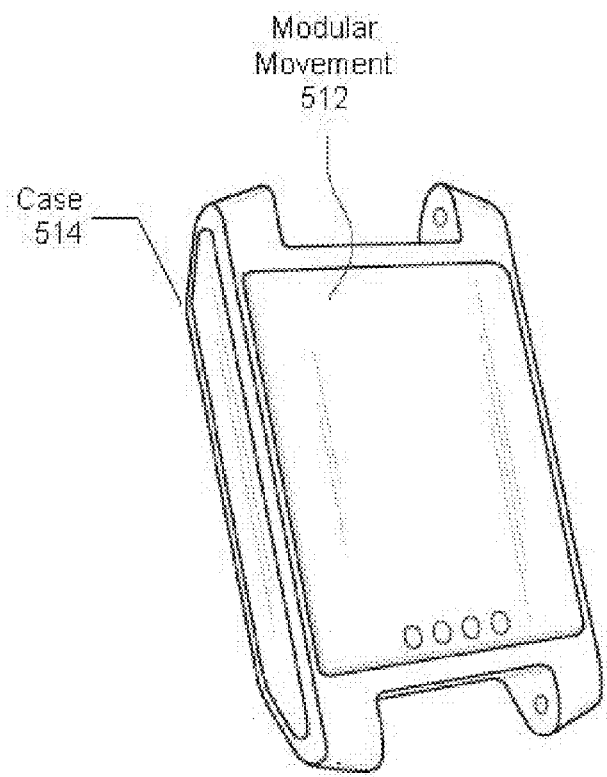

FIGS. 5A and 5B are diagrams illustrating an embodiment of the portable device. According to the exemplary embodiments, the portable device 510 may comprise a modular movement 512 (the "module") and a case 514. The module 512 includes a body 516 that houses a plurality of layers, including an integrated display (e.g., a touchscreen) and a movement subassembly 520, for displaying information, including time.

As used herein, the term "modular" means that the body 516 of the module 512 includes all parts necessary for operation and power of the module 512. Thus, the module 512 of the exemplary embodiment is fully functional in a standalone state. However, according to the exemplary embodiment, the case 514 of the portable device 510 includes a receptacle 522 for removably receiving the module 512 without need for a tool, such that the module 512 can be either used with the case 514 of the portable device 510 and/or is user interchangeable with the cases of other electronic devices having the same or similar types of receptacles.

The portable device 510 is shown as a wristwatch; however, various embodiments of the invention include other accessory forms. For example, some embodiments include other accessories with mounts for the module 512, such as mobile phones, computer bays, automobile mounts (e.g., dashboard mount, console mount), handheld games, media players (e.g., MP3 players), necklaces, brooches, belts, keyboards, cameras, bicycles, key chains, video cameras, speaker platforms, and ankle bracelets. In an alternative embodiment, the portable device 510 may be implemented as a stand-alone device, such as a cell phone, where the functions of module 512 including components of the below-described file sharing, are integrated into the stand-alone device.

In one exemplary embodiment, the module 512 and the receptacle 522 in the case 514 are made standard industry sizes, such that different modules 512 manufactured and sold by one set of manufacturers fit within the receptacles of different cases manufactured and sold by another set of manufacturers, for example.

In one embodiment, the receptacle 522 is formed as an opening in the back of the case 514 and the top or front of the case 514 includes an opening. In this embodiment, the module 512 is inserted into the case 514 from the bottom or back of the case 514, and once inserted the display of the module is visible through the opening in the top of the case 514. When the module 512 is used in a portable device 510, such as a watch, the display of the module 512 becomes the display of the portable device.

The display can include a display assembly including a color LCD display, a glass overlay and a touch-sensitive overlay. The display may form the top of the portable device 510 in an exemplary embodiment. In some embodiments, the display includes an active viewable area of 25.4 (H)× 25.4 (V) mm, with a display resolution between approximately 128 (H)×128 (V) and 200 (H)×200 (W) pixels. Other embodiments include other display resolutions. In some embodiments the display has an active area that measures less than 2.5" diagonally (in other embodiments, less than 2" diagonally).

As used herein, the portable device 510 may include a combination of both the case 514 and the module 512. But the term "case" 14 may denote the body of the portable device 510 into which the receptacle 522 is formed and into which the module 512 is to be inserted. According to another exemplary embodiment, the module 512 may be implemented as a computer-based electronic movement that is used to power the portable devices into which it is inserted.

A low computation computer method and system for determining a user's steps has been disclosed. The present invention described in accordance with the embodiments shown, and there could be variations to the embodiments, and any variations would be within the scope of the present invention. For example, the present invention can be implemented using hardware, software, a computer readable medium containing program instructions, or a combination thereof. Software written according to the present invention is to be either stored in some form of computer-readable medium such as memory or CD-ROM, and is to be executed by a processor. Accordingly, many modifications may be made without departing from the scope of the appended claims.

We claim:

1. A method for determining a user's steps by a portable device carried by a user, the method comprising:
    measuring, by at least one sensor of the portable device, raw sensor data including one or more of position, motion, tilt, shock or vibration, the at least one sensor including at least one inertial sensor;
    deriving amplitudes from the raw sensor data received from the at least one sensor of the portable device, by at least one processor of the portable device, the at least one processor including a first processor comprising a microcontroller unit (MCU);
    comparing, by a given one of the at least one processor, the amplitudes to an amplitude threshold, and counting a step when one of the amplitudes exceeds the amplitude threshold to obtain a step count, wherein if the amplitude threshold is not exceeded for a given amplitude, a step is not counted;
    determining, by a given one of the at least one processor, a current gait type based on the step count and a pace of the user's steps;
    dynamically adjusting, by a given one of the at least one processor, the amplitude threshold based on the current gait type to reduce false amplitude peaks in order to filter out swinging movements and false steps; and
    applying a post filter to the step count, by a given one of the at least one processor, based on time between steps and a minimum number of prior consecutive steps to derive a filtered step count, the filtered step count being used by the given processor to identify false readings due to short bursts of rapid movement by the user.

2. The method of claim 1, wherein the method is performed by the first processor of the at least one processor while a second processor of the at least one processor is in sleep mode, the method further comprising:
    as the second processor transitions from sleep mode to wake mode, outputting the filtered step count from the first processor to the second processor;
    calculating, by the second processor, a step rate and a step length using the filtered step counts; and
    calculating, by the second processor, any combination of distance traveled, speed, calories and pace using the step rate and step length and outputting to a display.

3. The method of claim 2 wherein:
    the second processor comprises a central processing unit (CPU);
    the MCU performs the deriving amplitudes from the raw sensor data received from the at least one sensor of the portable device; and
    the MCU only performs fixed-point arithmetic.

4. The method of claim 1, wherein deriving amplitudes further comprises:
    smoothing the amplitudes using a current amplitude and at least one previous amplitude to generate smoothed amplitudes.

5. The method of claim 4, further comprising: detecting peaks and troughs from the smoothed amplitudes.

6. The method of claim 4, wherein deriving amplitudes from raw sensor data further comprises:
receiving the raw sensor data as acceleration X, Y, Z values;
compositing the acceleration X, Y, Z values into a single magnitude value $M^2=X^2+Y^2+Z^2$; and
deriving a magnitude vector $V=M^2$ that is represented as a squared value, rather than a square root to minimize computations.

7. The method of claim 4, further comprising obtaining a smoothed magnitude vector corresponding to the current amplitude by assigning weights to the current amplitude and at least two previous magnitude vectors, adding the weighted amplitudes, and dividing the result, wherein division is implemented using a right shift so that little processing power is required.

8. The method of claim 7, further comprising: performing peak and trough detection to determine if the smooth magnitude vectors V are trending upward or trending downward by:
if a current V is greater than a previous V, then setting ascending mode, if the current V is less than previous V, then setting descending mode, and if the current V is the same as the previous V, ignore the current V and do not change mode; and
if in descending mode and switched to ascending mode, then determining a trough has been found, if in ascending mode and switched to descending mode, then determining a peak has been found, where an actual trough or crest is the previous V.

9. The method of claim 8, further comprising:
performing amplitude detection, wherein amplitude is calculated based on a difference between a peak and a preceding trough; and
comparing the amplitudes to the amplitude threshold.

10. The method of claim 1, wherein determining a current gait type based on the step count further comprises:
creating different amplitude thresholds for different gait types, wherein the gait types include a walking gait type, a fast walking gait type, a running gait type, and an unknown gait type; and
determining a gait type based on the step count; and
feeding the gait type back to a count estimator to improve accuracy of peak and trough determination of future counts.

11. The method of claim 10, wherein determining a gait type further comprises:
of past amplitudes, counting a number of small amplitudes (nSmalls) and a number of big amplitudes (nBigs);
if nBigs>2*nSmalls, then setting the gait type to a running gait type;
if nSmalls>2*nBigs, then setting the gait type to a walking gait type;
otherwise, if nBigs>3 and nSmalls>3, then setting the gait type to a fast walking gait type; and
otherwise, setting the gait type to an unknown gait type.

12. The method of claim 1, wherein the post filter further comprises:
if an elapsed time between a step in the previous step is less than a time threshold MAX_DELTA_T, then determining a current step is a candidate step; and
determining whether a number of consecutive candidate steps is greater than a consecutive steps threshold, if so, counting the candidate steps as true steps.

13. The method of claim 2, further comprising:
measuring the step rate from steps counted over time; and
calculating the speed as a log of the step rate.

14. The method of claim 13, further comprising:
calculating the step length as a delta from a base value determined from a height of the user.

15. A portable device configured to determine a user's steps, the portable device comprising:
an inertial sensor configured to measure raw sensor data including one or more of position, motion, tilt, shock or vibration;
a first processor coupled to the inertial sensor and configured to receive the raw sensor data from the inertial sensor; and
a step count component executing on the first processor, wherein the step count component is configured to:
derive amplitudes from the raw sensor data received from the inertial sensor;
compare the amplitudes to an amplitude threshold, and counting a step when one of the amplitudes exceeds the amplitude threshold to obtain a step count, wherein if the amplitude threshold is not exceeded for a given amplitude, a step is not counted;
determine a current gait type based on the step count and a pace of the user's steps;
dynamically adjust the amplitude threshold based on the current gait type to reduce false amplitude peaks in order to filter out swinging movements and false steps; and
apply a post filter to the step count based on time between steps and a minimum number of prior consecutive steps to derive a filtered step count, the filtered step count being used by the step count component to identify false readings due to short bursts of rapid movement by the user.

16. The portable device of claim 15, further comprising a second processor coupled to the first processor, and a display coupled to the second processor, wherein:
as the second processor transitions from sleep mode to wake mode, the first processor outputs the filtered step count to the second processor;
the second processor calculates a step rate and a step length using the filtered step counts; and
the second processor calculates any combination of distance traveled, speed, calories and pace using the step rate and step length for output to the display.

17. The portable device of claim 16 wherein:
the step count component comprises a microcontroller unit (MCU);
the second processor comprises a central processing unit (CPU);
the MCU is configured to perform the deriving amplitudes from the raw sensor data received from the inertial sensor; and
the MCU only performs fixed-point arithmetic.

18. The portable device of claim 15, wherein the step count component derives the amplitudes further by smoothing the amplitudes using a current amplitude and at least one previous amplitude to generate smoothed amplitudes.

19. The portable device of claim 18, wherein the step count component further detects peaks and troughs from the smoothed amplitudes.

20. The portable device of claim 18, wherein the step count component is configured to:
receive the raw sensor data as acceleration X, Y, Z values;
composite compositing the acceleration X, Y, Z values into a single magnitude value $M^2=X^2+Y^2+Z^2$;

derive a magnitude vector $V=M^2$ that is represented as a squared value, rather than a square root to minimize computations.

21. The portable device of claim 18, wherein a smoothed magnitude vector corresponding to the current amplitude is obtained by assigning weights to the current amplitude and at least two previous magnitude vectors, adding the weighted amplitudes, and dividing the result, wherein division is implemented using a right shift so that little processing power is required.

22. The portable device of claim 21, wherein the step count component is configured to perform peak and trough detection to determine if the smooth magnitude vectors V are trending upward or trending downward by:
if a current V is greater than a previous V, then set ascending mode, if the current V is less than previous V, then set descending mode, and if the current V is the same as the previous V, ignore the current V and do not change mode; and
if in descending mode and switched to ascending mode, then determine a trough has been found, and if in ascending mode and switched to descending mode, then determine a peak has been found, where an actual trough or crest is the previous V.

23. The portable device of claim 22, when the step count component is configured to perform amplitude detection, wherein amplitude is calculated based on a difference between a peak and a preceding trough; and the amplitudes are compared to the amplitude threshold.

24. The portable device of claim 15, wherein the step count component is configured to determine a current gait type based on the step count by:
create different amplitude thresholds for different gait types, wherein the gait types include a walking gait type, a fast walking gait type, a running gait type, and an unknown gait type; and
determine a gait type based on the step count; and
feed the gait type back to a count estimator to improve accuracy of peak and trough determination of future counts.

25. The portable device of claim 24, wherein the step count component is configured to determine a gait type by:
of past amplitudes, count a number of small amplitudes (nSmalls) and a number of big amplitudes (nBigs);
if nBigs>2*nSmalls, then set the gait type to a running gait type;
if nSmalls>2*nBigs, then set the gait type to a walking gait type;
otherwise, if nBigs>3 and nSmalls>3, then set the gait type to a fast walking gait type; and
otherwise, set the gait type to an unknown gait type.

26. The portable device of claim 15, wherein the step count component is configured to apply the post filter by:
if an elapsed time between a step in the previous step is less than a time threshold MAX_DELTA_T, then determine a current step is a candidate step; and
determine whether a number of consecutive candidate steps is greater than a consecutive steps threshold, if so, counting the candidate steps as true steps.

27. The portable device of claim 26, wherein the step count component is further configured to:
measure the step rate from steps counted over time; and
calculate the speed as a log of the step rate.

28. The portable device of claim 27, wherein the second processor is further configured to:
calculate the step length as a delta from a base value determined from a height of the user.

29. A computer readable storage device having executable program instructions for determining a user's steps, the program instructions, when executed by one or more processing devices of a portable client device including a microcontroller unit (MCU), causing the one or more processors to implement a method for determining a user's steps by the portable device, the method comprising:
measuring raw sensor data including one or more of position, motion, tilt, shock or vibration, the at least one sensor including at least one inertial sensor;
deriving amplitudes from the raw sensor data received from the at least one sensor of the portable device;
comparing the amplitudes to an amplitude threshold, and counting a step when one of the amplitudes exceeds the amplitude threshold to obtain a step count, wherein if the amplitude threshold is not exceeded for a given amplitude, a step is not counted;
determining a current gait type based on the step count and a pace of the user's steps;
dynamically adjusting the amplitude threshold based on the current gait type to reduce false amplitude peaks in order to filter out swinging movements and false steps; and
applying a post filter to the step count based on time between steps and a minimum number of prior consecutive steps to derive a filtered step count, the filtered step count being used to identify false readings due to short bursts of rapid movement by the user.

* * * * *